United States Patent
Ricci et al.

(10) Patent No.: US 6,777,227 B2
(45) Date of Patent: Aug. 17, 2004

(54) BIO-REACTOR AND CELL CULTURE SURFACE WITH MICROGEOMETRIC SURFACES

(76) Inventors: John L. Ricci, 46 Verdun Pl., Middletown, NJ (US) 07748; Harold Alexander, 47 Elmwood Pl., Short Hills, NJ (US) 07078; John Grew, 222 Edgewood Ter., South Orange, NJ (US) 07079

(*) Notice: Subject to any disclaimer, the term of this patent is extended or adjusted under 35 U.S.C. 154(b) by 0 days.

(21) Appl. No.: 10/338,076

(22) Filed: Jan. 7, 2003

(65) Prior Publication Data

US 2004/0077076 A1 Apr. 22, 2004

Related U.S. Application Data

(60) Provisional application No. 60/346,497, filed on Jan. 9, 2002.

(51) Int. Cl.[7] .............................................. C12M 1/24
(52) U.S. Cl. .......................... 435/304.1; 435/305.1; 435/305.2; 435/395
(58) Field of Search ...................... 435/299.1, 299.2, 435/304.1, 304.2, 304.3, 305.1, 305.2, 395; 623/16.11, 23.5, 23.76

(56) References Cited

U.S. PATENT DOCUMENTS

| 5,202,227 A | 4/1993 | Matsuda | |
|---|---|---|---|
| 5,645,740 A | * 7/1997 | Naiman et al. | 219/121.68 |
| 5,776,748 A | 7/1998 | Singhvi | |
| 5,833,641 A | 11/1998 | Curtis | |
| 5,855,608 A | * 1/1999 | Brekke et al. | 424/487 |
| 5,976,826 A | 11/1999 | Singhvi | |
| 6,027,695 A | * 2/2000 | Oldenburg et al. | 422/102 |
| 6,037,171 A | * 3/2000 | Larsson | 435/297.1 |

* cited by examiner

Primary Examiner—David A. Redding
(74) Attorney, Agent, or Firm—Melvin K. Silverman; Yi Li

(57) ABSTRACT

A bioreactor or cell culture surface comprises a multiplicity of microwells appearing, upon enlargement in the range of 200 to 1000 magnifications, as a honeycomb structure consisting of a plurality of rows of irregular hexagons, each having a transverse x-axis, a longitudinal y-axis, and a z-axis which defines a height of each microwell. Co-parallel major bases define the directionality of anticipated cell growth, while pairs of equilateral minor bases define the x-axis width of each microwell. An arrow-like geometry is defined by the equilateral pairs of minor bases which also define an x-axis separation between opposing major bases of the hexagon to induce cell growth directionality. An acute angle exists between the members of the arrow-like pairs of minor bases, while an obtuse angle exists between contiguous major and minor bases.

4 Claims, 3 Drawing Sheets

BIO-REACTOR AND CELL CULTURE SURFACE WITH MICROGEOMETRIC SURFACES

APPLICATION FOR LETTERS PATENT

BE IT KNOWN THAT We, John L. Ricci, Harold Alexander and John Grew, all citizens of the United States of America, have invented a certain new and useful improvement in a Bio-reactor and Cell Culture Surface with Microgeometric Features, of which the following is a Specification:

This application claims the benefit of provisional application No. 60/346,497, filed Jan. 9, 2002.

BACKGROUND OF THE INVENTION

A. Field of Invention

The present invention relates generally to the pattering of cell culture surfaces to maximize the ability of such surfaces to support adhesion, growth, colonization and differentiation of selectable cell lines.

B. Prior Art

Surface microgeometry plays a significant role in in vitro cell surface interactions as well as in in vivo tissue-implant surface interactions, although well-defined casual relationships are not yet fully established. For example, defined surface microgeometries such as grooved and machined metallic and polymer surfaces cause orientation of cells and matrix molecules thereof in vivo. See Chehroudi, et al "Titanium-coated micromachined grooves of different dimensions affect epithelial and connective tissue cells differentially in vivo," *Journal of BioMedical Materials Research,* 24:1203–1219 (1990), Matsuda, et al "Development of micropattering technology for cultured cells," Transactions of the American Society For Artificial Internal Organs, 36:M559-M562 (1990); Clark, et al, Topographical Control of Cell Behavior II. Multiple Grooved Substrates, *Development,* 108 (4) 1990; and Clark, et al, Cell Guidance by Ultra Fine Topography in vitro, Journal of Cell Science, 99 Part 1 (March 1991). It is further known that laser-microgrooved titanium surfaces can promote organized bone formation and integration around implants, and that surface texturing also enhances platelet attachment as well as fibrin clot adhesion, thereby improving the stability of implant tissue interface during colagenous matrix formation and contractrue during healing.

It is believed that surface texturing operates on multiple levels to improve implant stability and adhesion this, inter alia, due to the fact that textured surfaces have larger surface areas than do smooth surfaces, thus creating larger more stable mechanical interfaces. As such, textured surfaces also promote adhesion of fibrin and other, more permanent cell matrix components, and thus affect long term cell interactions at stable interfaces. In the short term, that is, soon after implantation, fibrous tissue cells are more organized and collagenous at smooth interfaces than at textured interfaces. This, of course, is not desirable given that fibrous cells constitute a principal component of scar tissue. In distinction, textured surfaces have the additional advantage over smooth surfaces of inhibiting colonization of fibrous tissue cells, also known as fibroblasts and of macrophagic cells which appear early during wound healing and normally encapsulate smooth substrates. It has also been recently shown that textured surfaces may also promote the differentiation of bone forming (oseogenic) cells which form at critical interfaces with implant surfaces.

More generically, and with particular reference to the subject matter of the instant invention, cell culture technology constitutes an essential tool for bio-materials and bio-medical engineering research as well as for basic science and bio-technical research. The controlled nature of the culture environment enables investigators to study cultured cells as experimental models, that is, microcosms, of actual living tissues. This technology is largely based on the propagation and analyzing of cells attached to culture substrates. However, most culturing occurs upon flat surfaces which, it has been demonstrated, promote rapid spreading of cells, uncontrolled cell growth, and the loss of cell differentiation, all of which impact upon the value of the culture environment as a tool of basic science and biotechnology research. There is therefore a need in the art for advanced culture surfaces that can be employed to control cell attachment, spreading, proliferation, and differentiation. The instant invention furthers these ends through the use of discrete surface microstructures based upon characteristics which are believed to be inherent to cell function and structure itself.

The invention is thereby particularly intended to provide a bio-reactor or cell culture surface which is more design specific for purposes of control of cell attachment, contact guidance, and cell shape, to a much higher degree than that in simple microgrooving of surfaces heretofore known in the art. The present invention is also significant in terms of modulation of the behavior of cultured mesenchymal stem cells as well as of differentiated connective tissue cell lines.

The prior art, as it relates to issued patents relative to cell culture surfaces, is reflected by U.S. Pat. No. 5,202,227 (1993) to Matsuda, et al, entitled Control of Cell Arrangement; and U.S. Pat. No. 5,976,826 (1999) to Singhvi, et al, entitled Device Containing Cytophilic Islands That Adhere Cells Separated By Cytiphobic Regions.

SUMMARY OF THE INVENTION

A bioreactor or cell culture surface comprises a multiplicity of microwells appearing, upon enlargement in the range of 200 to 1000 magnifications, as a honeycomb structure consisting of a plurality of rows of irregular hexagons, each having a transverse x-axis, a longitudinal y-axis, and a z-axis which defines a height of each microwell. Co-parallel major bases define the directionality of anticipated cell growth, while pairs of equilateral minor bases define the x-axis width of each microwell. An arrow-like geometry is defined by said equilateral pairs of minor bases which also define an x-axis separation between opposing major bases of the hexagon to induce cell growth directionality. An acute angle exists between the members of said arrow-like pairs of minor bases, while an obtuse angle exists between contiguous major and minor bases. The irregular hexagonal geometry also contributes to a convenient offset between x-axis rows of microwells relative to each other, so that tagging and observation thereof is simplified, and so that the potential for overgrowth of a cell or cell colony within a given microwell to an adjoining microwell of a different x-axis column of the cell culture surface is diminished. The depth of each microwell wall is preferably four micrometers, the x-axis width thereof in a range of 5 to 15 micrometers, and the y-axis length thereof in a range of 1 to 8 times said value of the width. The ratio of length to width, that is, the y/x aspect ratio, is typically in a range of 1:1 to 8:1 in which the thickness between adjacent major bases of adjacent microwells within a single x-axis column is one micrometer. Such cell culture surfaces can be formed using state of the art techniques such a photolithography, in etching, or polymer fabrication technology such as molding.

It is accordingly an object of the invention to provide an improved bioreaction and cell culture surface having microgeometric surface features specific to the modulation of cell growth and differentiation.

It is another object to provide a bioreactor of the above type capable of defining important cell dimension parameters for purposes of surface micrortextuing of anticipated orthopedic and other prosthetic devices.

It is a further object of the invention to provide an improved tool for the basic sciences associated with cellular research in terms of cell functions, inclusive of control of cell attachment, spreading, orientation, differentiation, and gene expression.

It is a yet further object to provide a bioreactor having a tissue-biomaterial interface permitting the fullest expression of mammalian cell types and their characteristics.

It is a still further object of the invention to provide a micro-formed substrate having particular utility as a cell culture tool and, more particularly, utility in the modulation of cultured mesenchymal stem cells and differentiated connective tissue cells.

It is another object to furnish a cell culture surface having particular use the study of the attachment, proliferation and differentiation of osteoblast-like cells.

It is another object of the invention to provide a bio-reactive surface of the above type that may be used to optimize design parameters for surfaces of implantable medical devices such as dental implants and total joint replacements.

It is a yet further object to provide a surface to provide a new and improved tool of basic research in cell biology.

It is a still further object of the invention to provide a cell culture surface of the above type having a surface chemistry to optimize ability of bio-medical substrates thereof to support the growth of osteogenic cells.

The above and yet other objects and advantages of the present invention will become apparent from the hereinafter set forth Brief Description of the Drawings and Detailed Description of the Invention.

DETAILED DESCRIPTION OF THE INVENTION

Figure 1:
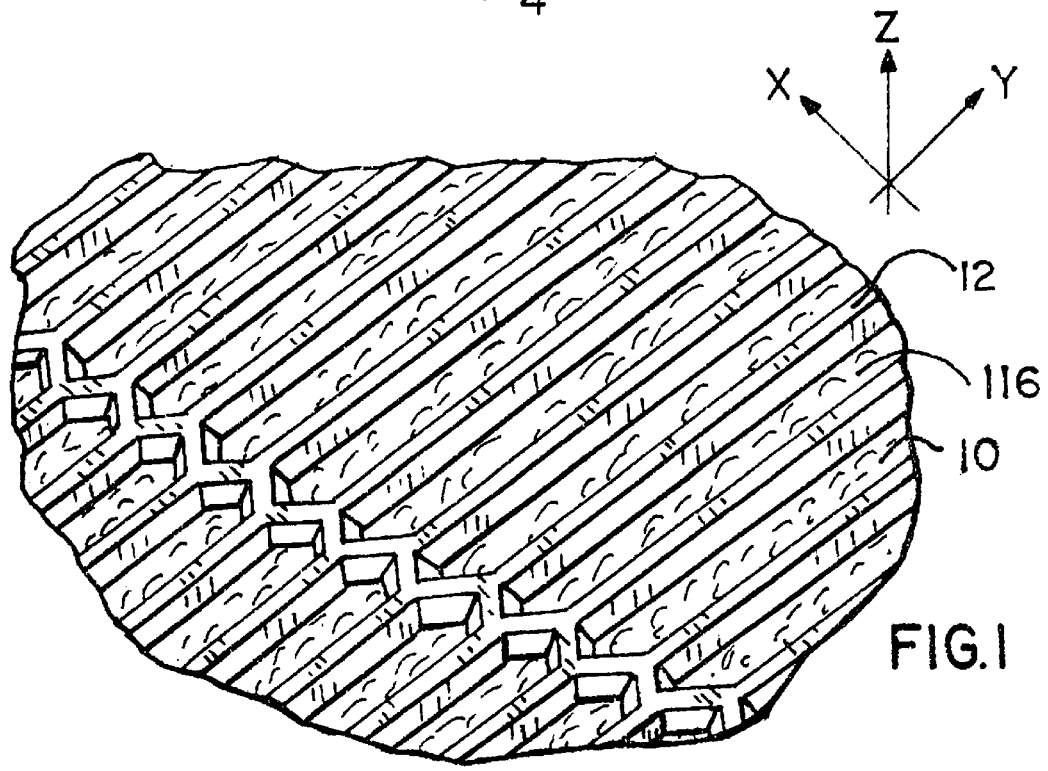
FIG. 1 is a perspective enlarged view at a magnification of about 1000 times of a bioreactor cell culture surface in accordance with the present invention, the same having an aspect ratio of 8/1.

With reference to the perspective view of FIG. 1, which represents an enlargement of about 1000 magnifications of the inventive bio-reactive cell culture surface 10, the same is characterized in terms of an x, y, z Cartesian coordinate system in which the x-axis represents the width of the bioreactor, the y-axis the length thereof, the z-axis the height of walls 12 thereof. The area of each microwell 116 is a function of the x and y dimensions thereof. As is shown in the top perspective view of FIG. 2, the cell culture surface 10 is seen to be defined by a plurality of x-axis columns 14 in which individual microwells 216 thereof define an irregular hexagonal geometry (more fully described below) such that an offset of one-half of a width of each micro-well exists between contiguous x-axis columns thereof. The result, as may be noted, somewhat resembles that of the wax honeycomb of a beehive.

Figure 2:
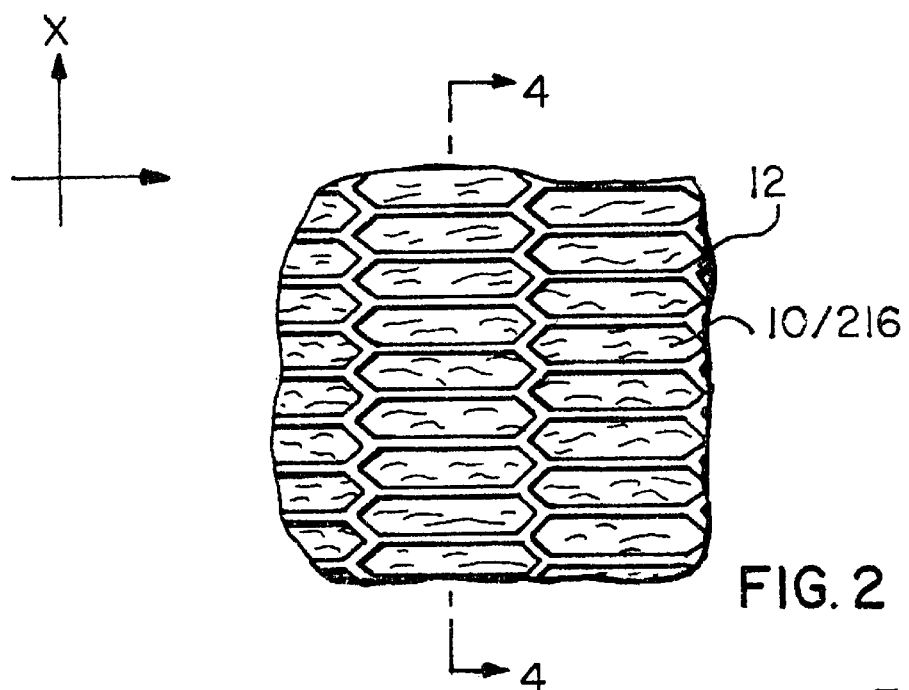
FIG. 2 is a top (xy plane) view of a cell culture surface in accordance with the present invention having an aspect ratio of 4/1 and showing the relationship of contiguous x-axis columns of microwells to each other.

In terms of materials, the structures of FIGS. 1 and 2 have been fabricated and tested with respect to titanium dioxide coated polystyrene, titanium alloys, and commercially-pure titanium implants. A silicon substrate may be used in lieu of polystyrene. It has been found that highly oriented, geometrically consistent microstructures may be achieved, upon such materials, through the use of computer controlled laser ablation techniques, as well as through state of the art photolithography followed by deep-reactive ion etching, particularly where a silicon wafer is employed as the substrate.

Figure 3:
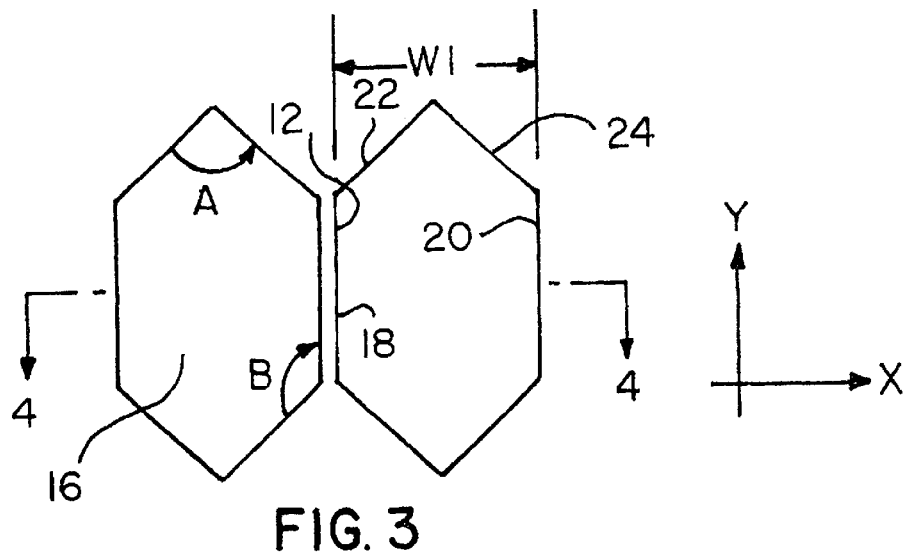
FIG. 3 is a top (xy plane) view of two x-axis contiguous microwells illustrating the irregular hexagonal geometry thereof.
Figure 4:
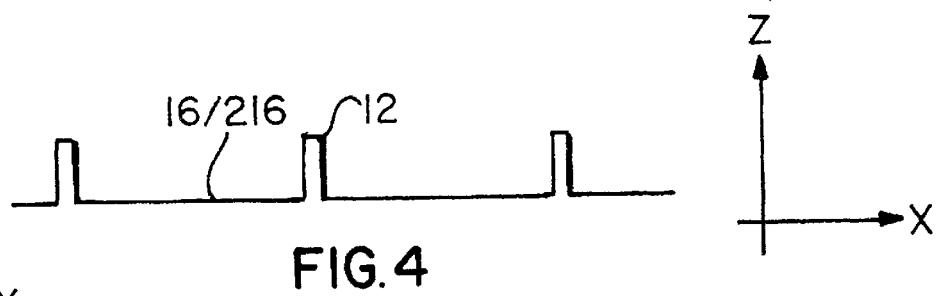
FIG. 4 is a vertical (xz plane) view taken along Line 4—4 of FIGS. 2 and 3.

The dimensionality of microwells 16/116/216 of the inventive structure may be more fully appreciated with reference to the views of FIGS. 3 thru 5. More particularly, there is shown in FIG. 3 two adjacent microwells 16 separated by said wall 12, said wells having a so-called aspect ratio of 2/1, meaning that the y-axis dimension is twice the x-axis of width dimension thereof. In FIG. 3, the width dimension is designated as W1. It may be appreciated that the microwells of the instant bioreactive surface will, in a preferred embodiment, comprise an irregular hexagon having opposing major bases 18 and 20 and, at y-axis ends of each microwell 16, pairs of arrow or triangular shaped minor bases 22 and 24, wherein contiguous major bases 18 and 20 thereof are separated by said microwell wall 12. In the 2/1 aspect ratio microwell 16 of FIG. 3, it has been determined that an angle A between the minor bases 22 and 24 will define an angle of 90 degrees or less, while an obtuse angle B defined between each major base 18/20 and its contiguous minor base 22/24 is preferably at least 135 degrees. A preferred x-axis separation between the microwells has been found to be about one micrometer, this comprising the width of walls 12 which, it has been found, are preferably about 4 micrometers in height.

With respect to the surface areas of the microwells 16/116/216 the same have been formed in areas of 250, 500, 1000 and 2000 square micrometers although it is believed that surface areas in excess of 1000 micrometers would require a W1 width in the x-axis in excess of 12 micrometers, that is, in excess of what is believed to be the optimal width for control of cell shape, attachment and growth parameters discussed above.

With reference to the xz plane (vertical) cross-sectional view of FIG. 4, the relative spacing of walls 12 to width W1 in the 2/1 aspect ratio of microwells 16 may be appreciated.

Figure 5A:
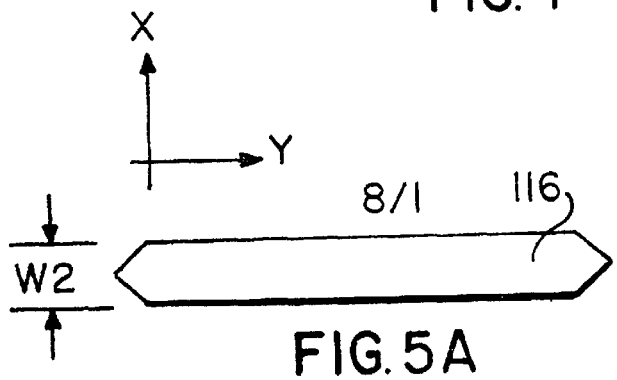
FIGS. 5A thru 5D are schematic views of the xy plane surface geometry of the cell culture surface showing microwells having aspect ratios of 8/1, 4/1, 2/1, and 1/1.

In FIGS. 5A thru 5D are shown other well aspect ratios which, it is believed, will have substantial application in the development of the instant technology and which will provide to the technology sufficient flexibility to study a wide variety of microstructural cell processes. More particularly, in FIG. 5A is shown the 8/1 aspect ratio microwell 116 (see also FIG. 1) having an x-axis width W2 of about six micrometers. Given a y-axis length of eight times that number, a resultant well base surface area of about 250 square micrometers occurs. If width W2 is increased to about 8 micrometers, the surface areas of well 116 is enlarged to about 500 square micrometers. Further, if width W2 is enlarged to about 12 micrometers, the area of the well will be increased to about 1000 square micrometers, and if width W2 is increased to about 16 micrometers, the surface area is increased to about 2000 square micrometers.

Figure 5B:
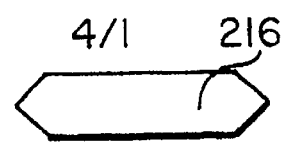

In FIG. 5B is shown the 4/1 aspect ratio microwell 216 (see also FIG. 2). Therein, because of the smaller ratio of length to width, that is, y/x ratio, a greater width W2 is required to achieve a like surface area of well 216 to that of the well 116 of FIG. 5A. More particularly, to achieve a base surface area of 250 square micrometers, well 216 must have a width W2 of about 8.5 micrometers and, to produce a base surface area of 500 square meters, must have a width of about 12 micrometers.

Figure 5C:
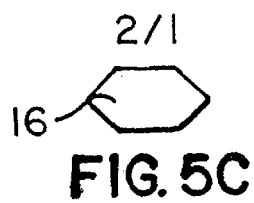

In FIG. 5C is shown the microwell 16 of FIG. 3, however, rotated 90 degrees relative thereof. In the 2/1 aspect ratio of microwell 16 of FIGS. 3 and 5C, the microwell must have an x-axis width of about 13 micrometers to produce base surface areas of about 250 square micrometers, and must have a width of about 18 micrometers to produce a base surface area of about 500 square micrometers.

Figure 5D:
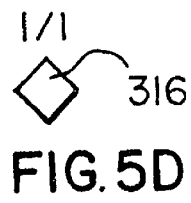

In FIG. 5D is shown a 1/1 aspect microwell 316 which, because its y-axis dimension requires an equal x-axis width (the hypotenuse of the structure), a width W2 of about 22 micrometers is needed to produce a base surface area of 250 square micrometers and of about 31 micrometers to produce a base surface area of about 500 square micrometers.

Figure 6:
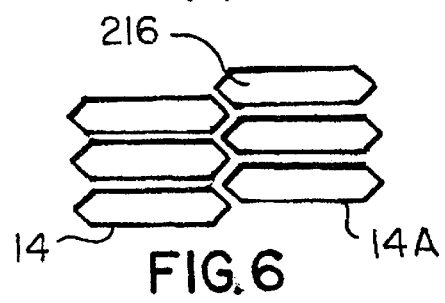
FIG. 6 is a top schematic view showing the relationship of respective x-axis columns of microwells and the interface between the minor bases of the hexagonal structures thereof.

In FIG. 6 is shown the relative disposition successive x-axis columns 14 and 14a of microwells 216, this in much the manner above shown in FIG. 2. It is to be appreciated that segmentation of individual microgrooves is reflected in the y-axis extent of each individual groove which, as well as the x-axis width, is essential to obtain meaningful data with reference to the numerous molecular, cellular and cytoskeletal parameters of cells necessary to explain their organizational structure, inherent shape, stability, contact guidance, response to mechanical stress, gene and signal protein activity, and apoptosis, this as set forth in the Objects of the Invention above. Otherwise, the widths W1 or W2 of each microgroove are intended to approximate the width of an elongate osteogenic, fibroblast, connective tissue, or mesenchymal stem cell during periods of growth. Given the elliptical geometry induced by growth upon controlled microgrooved surfaces, the length of the cell will typically exceed the width thereof by a ratio of between 2:1 and 5:1. Accordingly, in most research, cell enclosures defined by the microwells will mimic the cell lacunae itself. Stated otherwise, the present microwells of the instant invention are an effort to create a cell culture surface in which cells may be studied upon a substantially individual or discrete basis, and subject to their most natural morphology.

Figure 7:
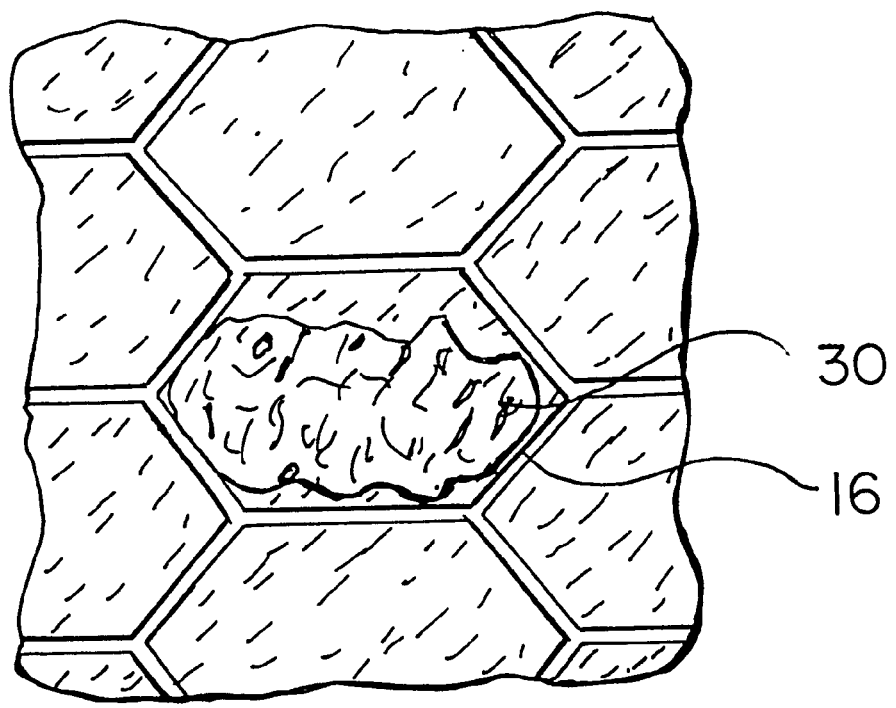
FIG. 7 is an electron micrograph of the invention showing cell growth at about 1000 magnifications.

An example of such discrete cell growth appears in the scanning electron micrograph of FIG. 7 in which a cell 30 is shown to have grown close to the wall-to-wall specification of the microwell 16 having a 2/1 aspect ratio. The capacity of microgrooves having essentially unlimited lengths, that is, those free of a geometry of compartmentalization, has been shown to establish a morphology and directionality of growth of large colonies of oseteogenic cells, this as is more particularly set forth in our Application Pending Ser. Nos. 09/500,038 and 09/784,284. However, the micrograph of FIG. 7 indicates that both x and y-axes of growth may be defined and are material for purposes of culture studies.

It has been determined that substrates suitable for formation of the microstructures above described include polystyrene as well as silicon, either of which may be coated with titanium dioxide, a titanium alloy, or a commercially-pure titanium, and formed by techniques both chemical, shown for example in U.S. Pat. No. 5,202,227 (1993) to Matsuda, as well as mechanical using lasers as is taught in U.S. Pat. No. 5,645,740 (1997) to Naiman, et al.

It is also contemplated that the above-described microstructure will have value upon curved as well as flat surfaces, this particularly within the context of surfaces of implants or prosthesis. In such application, the substrate itself may be formed of an acceptable biodegradable material adapted for resorption during a healing period.

It has thereby been discovered that microgeometry of the cell culture surface can significantly influence mitosis, differentiation, attachment, and cytosketal characteristics of the cell itself.

While there has been shown and described the preferred embodiment of the instant invention it is to be appreciated that the invention may be embodied otherwise than is herein specifically shown and described and that, within said embodiment, certain changes may be made in the form and arrangement of the parts without departing from the underlying ideas or principles of this invention as set forth herewith.

We claim:

1. A bioreactor comprising:

a cell culture surface having a multiplicity of microwells defining, upon enlargement in a range of 200 to 1000 magnifications, a honeycomb structure including a plurality of rows of irregular hexagons, each having a transverse x-axis, a longitudinal y-axis, and a z-axis which defines a depth of each microwell, in which parallel major bases of said hexagons define a directionality of anticipated cell growth, and pairs of equilateral minor bases define an x-axis width of each microwell, to thereby define an arrow-like geometry, in which said equilateral pairs of minor bases which also define an x-axis separation between opposing major bases of each hexagon to further induce cell growth directionality.

2. The bioreactor as recited in claim 1 in which:

an acute angle exists between said arrow-like geometry of said minor bases, and an obtuse angle exists between contiguous major and minor bases, whereby an irregular hexagonal geometry of said microwells contributes to a convenient offset between x-axis rows of microwells relative to each other, so that tagging and observation thereof is simplified, and the potential for overgrowth of a cell or cell colony within a given microwell to an adjoining microwell of a different x-axis column of said cell culture surface is diminished.

3. The bioreactor as recited in claim 2 in which:

said z-axis depth of each microwell wall comprises about four micrometers, said x-axis width thereof comprises about 5 to about 15 micrometers, and a y-axis length thereof comprises about 1 to about 8 times said value of said width.

4. The bioreactor as recited in claim 3 in which:

a y-to-x aspect ratio of length-to-width of each microwell comprises a range of about 1:1 to about 8:1, in which a thickness between adjacent major bases of adjacent microwells within a single x-axis now is about one micrometer.

* * * * *